US009085780B2

(12) United States Patent
Asano et al.

(10) Patent No.: US 9,085,780 B2
(45) Date of Patent: Jul. 21, 2015

(54) METHOD FOR INDUSTRIALLY PRODUCING (S)-1,1,1-TRIFLUORO-2-PROPANOL

(75) Inventors: Yasuhisa Asano, Imizu (JP); Kenichi Fuhshuku, Imizu (JP); Tetsuro Nishii, Kawagoe (JP); Akihiro Ishii, Kawagoe (JP)

(73) Assignees: Toyama Prefecture, Toyama-shi (JP); Central Glass Company, Limited, Ube-shi (JP)

( * ) Notice: Subject to any disclaimer, the term of this patent is extended or adjusted under 35 U.S.C. 154(b) by 86 days.

(21) Appl. No.: 13/519,058

(22) PCT Filed: Feb. 14, 2011

(86) PCT No.: PCT/JP2011/052981
§ 371 (c)(1),
(2), (4) Date: Jun. 25, 2012

(87) PCT Pub. No.: WO2011/099595
PCT Pub. Date: Aug. 18, 2011

(65) Prior Publication Data
US 2013/0005007 A1  Jan. 3, 2013

(30) Foreign Application Priority Data

Feb. 15, 2010 (JP) ................................. 2010-030365
Feb. 9, 2011 (JP) ................................. 2011-025966

(51) Int. Cl.
C12P 7/04 (2006.01)
C12N 1/16 (2006.01)
C12N 15/81 (2006.01)

(52) U.S. Cl.
CPC ... *C12P 7/04* (2013.01); *C12N 1/16* (2013.01); *C12N 15/81* (2013.01)

(58) Field of Classification Search
CPC .............. C12P 7/04; C12N 15/81; C12N 1/16
USPC .................... 435/157, 254.2, 254.22, 254.21
See application file for complete search history.

(56) References Cited

U.S. PATENT DOCUMENTS

2007/0009999 A1  1/2007  Doswald et al.
2009/0203096 A1  8/2009  Hayashi et al.

FOREIGN PATENT DOCUMENTS

| CN | 101218350 A | 7/2008 |
|---|---|---|
| CN | 101305098 A | 11/2008 |
| CN | 101501202 A | 8/2009 |
| EP | 1 945 785 B1 | 2/2010 |
| JP | 2009-501007 A | 1/2009 |
| JP | 2009-514542 A | 4/2009 |
| WO | WO 2007/006650 A2 | 1/2007 |
| WO | WO 2007/054411 A1 | 5/2007 |
| WO | WO 2007/142210 A1 | 12/2007 |

OTHER PUBLICATIONS

Buckholz et al Nature 1991, 9, pp. 1067-1072.*
Corresponding International Search Report with English Translation dated Mar. 15, 2011 (five (5) pages).
Form PCT/ISA/237 (four (4) pages), 2011.
Thomas C. Rosen et al., "Biocatalyst vs. Chemical Catalyst for Asymmetric Reduction", Supplement to Chimica Oggi, Chemistry Today, 2004, pp. 43-45.
M. Bucciarelli et al., "Asymmetric Reduction of Trifluoromethyl and Methyl Ketones by Yeast; An Improved Method", Synthesis, vol. 11, 1983, pp. 897-899.
Thomas C. Rosen et al., "Bioreductive Synthesis of Perfluorinated Chiral Alcohols", Elsevier, Tetrahedron Letters, vol. 47, 2006, pp. 4803-4806.

* cited by examiner

*Primary Examiner* — Tekchand Saidha
*Assistant Examiner* — Md. Younus Meah
(74) *Attorney, Agent, or Firm* — Crowell & Moring LLP

(57) ABSTRACT

Disclosed is a method for producing (S)-1,1,1-trifluoro-2-propanol with high optical purity and high yield by having at least one kind of microorganism, which is selected from the group consisting of *Hansenula polymorpha, Pichia anomala, Candida parapsilosis, Candida mycoderma, Pichia naganishii, Candida saitoana, Cryptococcus curvatus, Saturnospora dispora, Saccharomyces bayanus* and *Pichia membranaefaciens*, act on 1,1,1-trifluoroacetone. Since microorganisms found in nature are made to act in a natural state, the problems to be raised when a transformant or the like is used can be avoided in this method. Consequently, the method can be easily put in industrial practice.

7 Claims, No Drawings

METHOD FOR INDUSTRIALLY PRODUCING (S)-1,1,1-TRIFLUORO-2-PROPANOL

TECHNICAL FIELD

The present invention relates to a method for industrially producing (S)-1,1,1-trifluoro-2-propanol which is important as an intermediate for medicines and agrichemicals.

BACKGROUND ART (S)-1,1,1-Trifluoro-2-propanol is a compound important as an intermediate for various medicines and agrichemicals. Aside from methods using chemical catalysts, biological methods of reducing 1,1,1-trifluoroacetone to (S)-1,1,1-trifluoro-2-propanol by having microbial enzymes act on 1,1,1-trifluoroacetone has hitherto been studied. For example, Patent Document 1 discloses a method for producing (S)-1,1,1-trifluoro-2-propanol with high enantiomeric excess of not smaller than 99% ee by enantioselective reduction of 1,1,1-trifluoroacetone with use of alcohol dehydrogenases, and Patent Document 2 discloses a method for producing 93 to 99% ee of (S)-1,1,1-trifluoro-2-propanol by reducing 1,1,1-trifluoroacetone with use of a commercially available dried bakers' yeast. Additionally, Patent Document 3 discloses a method for production of (S)-1,1,1-trifluoro-2-propanol, which comprises the step of reacting 1,1,1-trifluoroacetone with a microorganism capable of functionally developing an enzyme such as an alcohol dehydrogenase, a carbonyl reductase and the like, or a transformant, or a treated product of these.

Meanwhile, in Non-Patent Document 1, there is disclosed that (S)-1,1,1-trifluoro-2-propanol can be produced with about 80% ee optical purity by reducing 1,1,1-trifluoroacetone with use of a dried bakers' yeast. Additionally, Non-Patent Document 2 discloses a method for producing (S)-1,1,1-trifluoro-2-propanol by reducing 1,1,1-trifluoroacetone with use of an alcohol dehydrogenase.

PRIOR ART DOCUMENTS

Patent Documents

Patent Document 1: International Publication No. 2007/054411
Patent Document 2: International Publication No. 2007/006650
Patent Document 3: International Publication No. 2007/142210

Non-Patent Documents

Non-Patent Document 1: M. Buccierelli et al., Synthesis, Vol. 11, p. 897-899, 1983
Non-Patent Document 2: T. C. Rosen et al., Chimica Oggi Suppl, p. 43-45, 2004

SUMMARY OF THE INVENTION

The methods of Patent Documents 1 and 3 and Non-Patent Document 2 employ a transformant formed by introducing a specified gene into a microorganism, thereby obtaining (S)-1,1,1-trifluoro-2-propanol of high optical purity. However, the transformant is formed by introducing a gene at random so as to sometimes be attended with an unexpected character; therefore, there has been concerned the risk where a resultant derived from such a transformant is incorporated as an impurity into a product. Furthermore, in the case where the resultant is dispersed in nature, there arises a fear of an influence on wildlife. Thus it has been necessary to establish the safety and to provide particular facilities for preventing the dispersion of the above-mentioned microorganism, so that it has not always been easy to put the methods in practice.

The method of Patent Document 2 employs a commercially available dried bakers' yeast and hence does not need its own culture equipment, so that the microorganism can be readily available. However, it is difficult to say that the method is high in efficient at a desired reduction reaction since this method requires the amount of the microorganism of 10 times larger than that of a substrate for reaction, and additionally a massive amount of waste has also raised issues. Moreover, a heat treatment of microorganism is needed in order to obtain a target compound with high optical purity, so that, on the assumption that the scale is a large one, a delicate temperature control required therein is so hard that the method has been difficult to employ in industrial terms.

In the method of Non-Patent Document 1, the optical purity is low and more specifically about 80% ee, and additionally, the amount of the microorganism is required to be not less than 300 times larger than that of a substrate. Hence this is a method difficult to employ in terms of practicability and productivity.

An object of the present invention is to provide a method for economically and conveniently producing (S)-1,1,1-trifluoro-2-propanol on an industrial scale.

The present inventors had eagerly made studies in order to attain the above object. As a result, they found a method that can produce (S)-1,1,1-trifluoro-2-propanol with high optical purity, high yield and an industrially adoptable yield by having a certain microorganism act on 1,1,1-trifluoroacetone, thereby having completed the present invention.

More specifically, the present invention provides inventions as will be discussed in the following [Invention 1] to [Invention 7].

[Invention 1]

A method for producing (S)-1,1,1-trifluoro-2-propanol or a production method for obtaining (S)-1,1,1-trifluoro-2-propanol represented by the formula

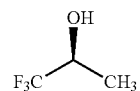

[2]

by having a microorganism act on 1,1,1-trifluoroacetone represented by the formula [1], the microorganism being found in nature and used in a natural state,

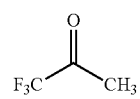

[1]

the method being characterized by using as the microorganism at least one kind of microorganism, which is selected from the group consisting of *Hansenula polymorpha*, *Pichia anomala*, *Candida parapsilosis*, *Candida mycoderma*, *Pichia naganishii*, *Candida saitoana*, *Cryptococcus curvatus*, *Saturnospora dispora*, *Saccharomyces bayanus* and *Pichia membranaefaciens*.

[Invention 2]

A method for producing (S)-1,1,1-trifluoro-2-propanol, as discussed in Invention 1, characterized in that the microorganism is provided with an accession number as shown below.

TABLE 1

| Microorganism | Accession Number |
| --- | --- |
| Hansenula polymorpha | NBRC0799, ATCC26012 |
| Pichia anomala | NBRC0120 |
| Candida parapsilosis | NBRC0708 |
| Candida mycoderma | NBRC1247 |
| Pichia naganishii | NBRC1670 |
| Candida saitoana | NBRC0380 |
| Cryptococcus curvatus | NBRC1159 |
| Saturnospora dispora | NBRC0035 |
| Saccharomyces bayanus | NBRC0676 |
| Pichia membranaefaciens | NBRC0128 |

[Invention 3]

A method for producing (S)-1,1,1-trifluoro-2-propanol, as discussed in Invention 1 or 2, characterized in that a suspension of the microorganism which is found in nature and in a natural state is prepared in such a manner that the microorganism has a density of from $10^7$ to $10^{11}$ cfu/ml and in that 1,1,1-trifluoroacetone is added to the prepared suspension so that the acetone has a concentration of from 0.05 to 3% (w/v).

[Invention 4]

A method for producing (S)-1,1,1-trifluoro-2-propanol, as discussed in any one of Inventions 1 to 3, characterized in that the reaction temperature is within a range of from 20 to 30° C.

[Invention 5]

A method for producing (S)-1,1,1-trifluoro-2-propanol, as discussed in any one of Inventions 1 to 4, characterized in that the pH during the reaction is within a range of from 6.0 to 9.0.

[Invention 6]

A method for producing (S)-trifluoro-2-propanol, as discussed in any one of Inventions 1 to 5, characterized in that a coenzyme NAD(P)H used for a reduction reaction is regenerated by virtue of a dehydrogenase of the microorganism itself, without a further addition of coenzyme NAD(P)H from the outside.

[Invention 7]

A method for producing (S)-1,1,1-trifluoro-2-propanol, as discussed in any one of Inventions 1 to 6, characterized in that glucose is used as a substrate for the dehydrogenase in regeneration of the coenzyme NAD(P)H.

As discussed above, a production method for obtaining (S)-1,1,1-trifluoro-2-propanol by having a microorganism act on 1,1,1-trifluoroacetone to cause reduction has conventionally widely been known. However, this method requires the use of a transformant and a heat treatment on the microorganism in order to obtain a high optical purity, and there is a case necessitating a large amount of microorganism at the time of reaction, so that this method has been difficult to adopt as an industrial production method. In view of the above, the present inventors have found that it is possible to conveniently produce (S)-1,1,1-trifluoro-2-propanol with high optical purity on an industrial scale by: selecting a specific microorganism (also) referred to as "a cell body") inherently having an ability to reduce 1,1,1-trifluoroacetone to (S)-1,1,1-trifluoro-2-propanol with high optical purity, among microorganisms found in nature; adding 1,1,1-trifluoroacetone to a suspension of the microorganism which is in a natural state in such a manner that the concentration of 1,1,1-trifluoroacetone is 0.01 to 5% (w/v), the suspension being prepared to have a density of $10^6$ to $10^{12}$ cfu/ml; and then initiating a reaction at a reaction temperature of from 5 to 40° C. at pH 4.0 to pH 10.0. Furthermore, the present invention is able to regenerate a coenzyme NAD(P)H used for the reduction reaction by virtue of a dehydrogenase that the microorganism itself has and therefore does not need to add an additional coenzyme NAD(P)H from the outside, which is one of preferable embodiments (as a matter of course, the reaction may also proceed even with the addition of the coenzyme NAD(P)H).

"The microorganisms found in nature" mentioned herein refers to cells on which genetic engineering such as transformation has not been conducted, and more specifically to wild strains preserved by various microorganism depositary organizations. Additionally, "a natural state" refers to a state where a cultured microorganism is used as it is, and more specifically to a state where neither an operation for breaking the microorganism to separate enzymes nor a cell treatment such as heat treatment, chemical agent treatment and the like is conducted.

Through the present invention, there can be obtained a greatly useful finding that a yield per production batch is significantly improved as compared with that in conventional techniques by providing the microorganism with a specified density and providing 1,1,1-trifluoroacetone with a specified concentration, thereby accomplishing a large-scale economical production.

In the present invention, the concentration of 1,1,1-trifluoroacetone refers to the concentration (w/v) of the acetone in a suspension of the microorganism (the concentration of a product obtained upon reduction is not taken into account or is excluded) and it is not such as to prescribe the total amount of the addition of the acetone in all of the reaction.

Though details will be discussed below, there can also be obtained a preferable finding that the reaction comes to smoothly proceed with the addition of glucose prepared to have a specified concentration.

A finding similar to that obtained by the present invention, i.e., a finding that (S)-1,1,1-trifluoro-2-propanol of high optical purity (up to 100% ee) can be produced on an industrial scale by: selecting a microorganism that should inherently provide a target compound with high optical purity, among microorganisms found in nature; using cultured cells as they are for the reaction; and having 1,1,1-trifluoroacetone react with a cell suspension prepared to have a specified range of density, within a specified temperature range, has not hitherto been known at all.

DETAILED DESCRIPTION OF THE INVENTION

It is possible to produce (S)-1,1,1-trifluoro-2-propanol which is important as an intermediate for medicines and agrichemicals, industrially conveniently and efficiently.

A microorganism used in the present invention is such as to be able to efficiently stereoselectively reduce a carbonyl group of 1,1,1-trifluoroacetone to a hydroxyl group. By having contrived a method for adding a substrate 1,1,1-trifluoroacetone at a concentration suitable for the reaction, (S)-1,1,1-trifluoro-2-propanol that had been difficult to industrially product becomes allowed to be provided with high optical purity and high yield.

Hereinafter, the present invention will be discussed in detail. 1,1,1-Trifluoroacetone used in the present invention is a publicly known compound and therefore it is possible to use either one that the skilled in the art prepares based on conventional techniques or commercially available one.

In the present invention, as 1,1,1-trifluoroacetone, it is possible to use the compound itself as a matter of course, and similarly it is also possible to use adducts formed between the compound and water or alcohols having 1 to 4 carbon atoms. When the above-mentioned reaction conditions are adopted, a microorganism with which (S)-1,1,1-trifluoro-2-propanol can be obtained is exemplified by at least one kind selected from the group consisting of *Hansenula polymorpha, Pichia anomala, Candida parapsilosis, Candida mycoderma, Pichia naganishii, Candida saitoana, Cryptococcus curvatus, Saturnospora dispora, Saccharomyces bayanus* and *Pichia membranaefaciens*, preferably from the group consisting of *Hansenula polymorpha, Candida parapsilosis, Saturnospora dispora, Saccharomyces bayanus* and *Pichia membranaefaciens*, and much more preferably *Hansenula polymorpha* or *Pichia membranaefaciens*.

These microorganisms have been provided with respective accession numbers as shown below and deposited in various organizations. Incidentally, these microorganisms are commercially available and therefore the skilled in the art can obtain them easily.

TABLE 2

| Microorganism | Accession Number | Depositary Organization |
| --- | --- | --- |
| Hansenula polymorpha | NBRC0799, ATCC26012 | National Institute of Technology and Evaluation, American Type Culture Collection |
| Pichia anomala | NBRC0120 | National Institute of Technology and Evaluation |
| Candida parapsilosis | NBRC0708 | National Institute of Technology and Evaluation |
| Candida mycoderma | NBRC1247 | National Institute of Technology and Evaluation |
| Pichia naganishii | NBRC1670 | National Institute of Technology and Evaluation |
| Candida saitoana | NBRC0380 | National Institute of Technology and Evaluation |
| Cryptococcus curvatus | NBRC1159 | National Institute of Technology and Evaluation |
| Saturnospora dispora | NBRC0035 | National Institute of Technology and Evaluation |
| Saccharomyces bayanus | NBRC0676 | National Institute of Technology and Evaluation |
| Pichia membranaefaciens | NBRC0128 | National Institute of Technology and Evaluation |

In culture of the above-mentioned microorganisms, it is possible to use culture media (solid media or liquid media) containing nutritional components used for ordinary microbiological culture; however, in the case of conducting a reduction reaction of 1,1,1-trifluoroacetone which is water-soluble, it is preferable to adopt liquid media. The culture media are formed containing: a carbon source such as sugars e.g. glucose, sucrose, maltose, lactose, fructose, trehalose, mannose, mannitol, dextrose and the like, alcohols e.g. methanol, ethanol, propanol, butanol, pentanol, hexanol, glycerol and the like and organic acids e.g. citric acid, glutamic acid, malic acid and the like; and a nitrogen source such as ammonium salt, peptone, polypeptone, casamino acid, urea, yeast extract, malt extract, corn steep liquor and the like. Furthermore, the addition of other nutritional sources such as inorganic salts and the like e.g. potassium dihydrogenphosphate, dipotassium hydrogen phosphate and the like is acceptable.

Among these carbon sources, nitrogen sources and inorganic salts, the carbon sources are preferably added in an amount which is sufficient for the growth of a microorganism and in an amount which does not inhibit the growth. Ordinarily 5 to 80 g, preferably 10 to 40 g of the carbon sources is added relative to 1 L of a culture medium. This is the same to the nitrogen sources, and more specifically, it is preferable to add the nitrogen sources in an amount sufficient for the growth of the microorganism and in an amount which does not inhibit the growth. The amount is ordinarily 5 to 60 g and preferably 10 to 50 g relative to 1 L of a culture medium. The inorganic salts that serve as a nutritional source require the addition of an element necessary for the growth of the microorganism. When its concentration is high, the growth of the microorganism becomes inhibited, so that it is added in an amount of from 0.001 to 10 g relative to 1 L of the culture medium. Incidentally, these may be used in combination of two or more kinds according to microorganisms.

The pH of the culture medium is required to be adjusted within a range suitable for the growth of the microorganism, and more specifically it is ordinarily from 4.0 to 10.0, preferably from 6.0 to 9.0. The temperature range during culture is required to be adjusted within a range suitable for the growth of the microorganism, and more specifically it is ordinarily from 10 to 50° C., preferably from 20 to 40° C. During culture, the culture medium desires air ventilation of preferably from 0.3 to 4 vvm ("vvm" refers to the amount of ventilation per 1 minute relative to the volume of the culture medium, or to volume/volume/minute) and more preferably from 0.5 to 2 vvm. On a microorganism that requires a large amount of oxygen, ventilation may be conducted in an air having an increased oxygen concentration by using an oxygen generator or the like. Concerning an equipment difficult to arbitrarily determine the amount of ventilation, such as a test tube, a flask and the like, it is possible to set the amount of the culture medium at 20% or lower relative to the volume of the equipment and to provide the equipment with a vent plug such as a cotton plug, a silicon plug and the like. In order to develop culture smoothly, it is preferable to stir the culture medium. In the case of using a fermenter, stirring is performed preferably at 10 to 100%, more preferably at 20 to 90% of a stirring ability of this apparatus. Meanwhile, when a small-scale equipment such as a test tube, a flask and the like is used, it is preferable to conduct stirring in the use of a shaker at 50 to 300 rpm, more preferably at 100 to 250 rpm. The culture time is required only to be one by which the growth of the microorganism has settled down, and it is preferably from 6 to 72 hours, more preferably from 12 to 48 hours.

In order to have the microorganism act on the substrate 1,1,1-trifluoroacetone, it is ordinarily possible to use a suspension with which the microorganism has been cultured, for the reaction as it is. If a component produced during culture adversely affect the reduction reaction, cells may be once isolated from a liquid medium through an operation such as centrifugal separation and the like and the suspension may be prepared again with the thus obtained cells (wet cell bodies) to be used for the reaction.

In order to develop the reaction efficiently, it is necessary to increase the density of the cells in the suspension. However, an excessively increased density sometimes inhibits the reaction due to generation of autolytic enzymes, accumulation of final metabolites and the like, so that the density is ordinarily from $10^6$ to $10^{12}$ cfu/ml ("cfu" refers to colony forming units that mean the number of colonies formed on an agar culture medium), preferably from $10^7$ to $10^{11}$ cfu/ml, and more preferably from $10^8$ to $10^{10}$ cfu/ml.

Regarding the addition of 1,1,1-trifluoroacetone to the suspension, the acetone is required to be kept having a concentration that smoothly develops the reduction reaction while not adversely affecting the existence of the microorganism. For example, a concentration higher than 5% (w/v) sometimes brings the microorganism extinct or reduces the optical purity, so that the concentration is ordinarily lower than the above-mentioned value, i.e., from 0.01 to 5% (w/v), and preferably from 0.05 to 3% (w/v). As the grounds for the capacity to calculate the acetone concentration, for example, it is possible to consider the amount of a liquid medium charged into a test tube before steam sterilization (Example 1) and the total amount of the suspension of the microorganism after culture (Example 3), as an index. Additionally, regarding a method for adding 1,1,1-trifluoroacetone to the suspension, it is preferable to conduct the addition sequentially in such a manner as to maintain a preferable range while monitoring the reduction reaction. With regard to the total amount of the addition of 1,1,1-trifluoroacetone, its preferable range is required to be adjusted according to microorganisms since there is a concentration at which the reaction settle down due to accumulation of products; however, it is preferably from 0.1 to 30% (w/v), more preferably from 0.2 to 20% (w/v) relative to the suspension.

The reaction temperature is required to maintain a range suitable for an enzyme reaction of a selected microorganism and therefore it is ordinarily from 5 to 40° C., preferably from 20 to 30° C. Moreover, the pH during the reaction is also required to maintain a range suitable for an enzyme reaction of a selected microorganism and therefore it is ordinarily from 4.0 to 10.0, preferably from 6.0 to 9.0.

The suspension, if it is in a state allowed to stand still, is reduced in reaction efficiency since the microorganism is sedimentated. Hence the reaction is conducted while stirring the suspension. Moreover, ventilation is needed for supplying oxygen sufficient for the microorganism to breath, but an excessively large amount of ventilation disperses 1,1,1-trifluoroacetone and (S)-1,1,1-trifluoro-2-propanol out of the system as gas; accordingly, ventilation is preferably conducted at 0.3 vvm or less, more preferably at 0.1 vvm or less. The reaction time is determined by the degree of formation of a target compound and is ordinarily from 6 to 312 hours.

In the present invention, a coenzyme NAD(P)H (a hydrogen donor) used for the reduction reaction can be regenerated from a coenzyme NAD(P) in the use of a dehydrogenase that the microorganism has. Hence it is preferable to conduct the reduction reaction upon having glucose separately exist in the suspension. Herein it is also possible to use sugars other than glucose, and alcohols; for example, sugars and alcohols discussed in the section of microbiological culture as carbon sources are usable. Glucose may directly be added to the cell suspension or may be added to the suspension upon previously being mixed with the substrate 1,1,1-trifluoroacetone. As the coenzyme NAD(P)H, a commercially available one may separately be added to conduct the reduction reaction, but it is so costly as not to be economical.

The present inventors have obtained a greatly desirable finding that the number of reductions per one cell is increased by having a microorganism itself cause regeneration without a further addition of coenzyme NAD(P)H from the outside thereby allowing the target compound to be produced with good cost efficiency and high productivity. By using a coenzyme NAD(P)H (that the microorganism itself possesses in its cells) as it is, NAD(P) to be generated after the reaction becomes allowed to be regenerated into the coenzyme NAD(P)H by virtue of the dehydrogenase of the microorganism itself. Incidentally, "without a further addition of coenzyme NAD(P)H from the outside" discussed herein refers to a state where the amount of the coenzyme NAD(P)H is less than 1 μmol/L relative to the liquid medium. The amount of the coenzyme NAD(P)H is more preferably less than 0.1 μmol/L (exclusive of the coenzyme that the cells possess).

Thus, an embodiment of producing the target compound without purposely adding the coenzyme NAD(P)H to the reaction system is typical of "regenerating the coenzyme NAD(P)H by the dehydrogenase of the microorganism itself without a further addition of coenzyme NAD(P)H from the outside", which is extremely preferable.

Glucose used herein as an additive is required to be added in an amount not inhibiting the reaction, and preferably so added as to maintain the concentration in the suspension at 0.1 to 10% (w/v). For example, as will be discussed below in Example 4, the reaction is conducted while constantly maintaining a glucose concentration of 2% in the reaction system by using a concentration controller equipped with a sugar concentration sensor and the like, which is one of particularly preferable embodiments of the present invention from the fact that the reaction proceeds smoothly.

An object of the method of the present invention is to be a production method which is industrial at the time of converting 1,1,1-trifluoroacetone into (S)-1,1,1-trifluoro-2-propanol, in which a mass production is accomplished by adopting suitable reaction conditions.

Incidentally, the present invention is able to provide an alcohol taking on an S-configuration, i.e., (S)-1,1,1-trifluoro-2-propanol, with a practically adoptable optical purity of not smaller than 85% ee, more preferably of not smaller than 98% ee.

In recalling a produced (S)-1,1,1-trifluoro-2-propanol from a final reaction solution, it is possible to adopt an isolation method general in organic synthesis. By performing a usual post-treatment operation such as extraction using organic solvents and the like after the reaction has terminated, a crude product is obtained. In particular, by subjecting a final reaction solution or a filtrate obtained after filtering out the cells as needed to distillation directly, it becomes possible to recall (S)-1,1,1-trifluoro-2-propanol with convenience and high yield. The thus obtained crude product may be subjected to a purification operation such as dehydration, activated carbon, distillation, recrystallization, column chromatography and the like. Furthermore, it is also possible to conduct an operation for enhancing the optical purity of the obtained product.

Examples will be discussed below; however, the present invention is not limited by the following Examples.

EXAMPLE 1

Results of Examination (Screening) of Reactivity to 1,1,1-Trifluoroacetone

A liquid medium was prepared to be composed of 1000 ml of an ion-exchanged water, 10 g of glucose, 5 g of polypeptone, 3 g of yeast extract, 3 g of malt extract, 3 g of potassium dihydrogenphosphate and 2 g of dipotassium hydrogen phosphate. The liquid medium was charged into test tubes 41.4 cm×18 cm) in an amount of 5 ml each, and then subjected to steam sterilization at 121° C. for 15 minutes.

These liquid media were inoculated with microorganisms shown in Table 3 and then shake culture was conducted thereon at 28° C. for 24 hours, thereby preparing suspensions ranging from $1.0 \times 10^9$ to $5.0 \times 10^9$ cfu/ml. To each of the cell suspensions, 0.5% (25 μl) of 1,1,1-trifluoroacetone and 250 μl of 1M glucose were added, and then shake culture was conducted thereon at 28° C. for 24 hours to develop reaction. After the reaction, n-butyl acetate was added to each reaction solution and mixed, followed by centrifugal separation to separate a layer of n-butyl acetate. The thus obtained n-butyl acetate layer was measured in terms of the optical purity of a product according to analyzing conditions as mentioned later, the result of which is shown in Table 3.

TABLE 3

| Microorganism and Accession Number | Optical Purity |
|---|---|
| *Hansenula polymorpha* NBRC0799 | 100% ee (S) |
| *Saturnospora dispora* NBRC0035 | 100% ee (S) |
| *Candida saitoana* NBRC0380 | 98.8% ee (S) |
| *Cryptococcus curvatus* NBRC1159 | 98.3% ee (S) |
| *Saccharomyces bayanus* NBRC0676 | 100% ee (S) |
| *Pichia membranaefaciens* NBRC0128 | 100% ee (S) |

Thus, it can be confirmed from above that (S)-1,1,1-trifluoro-2-propanol was produced with high enantiomeric excess in any cases using *Hansenula polymorpha* NBRC0799, *Saturnospora dispora* NBRC0035, *Candida saitoana* NBRC0380, *Cryptococcus curvatus* NBRC1159, *Saccharomyces bayanus* NBRC0676 and *Pichia membranaefaciens* NBRC0128.

[Analyzing Conditions]

Analysis of the optical purity was carried out by gas chromatography. As a column for gas chromatography, BGB-174 (30 m×0.25 mm×0.25 mm) manufactured at BGB Analytik AG was used. A carrier gas was helium. The pressure was 100 kPa. The temperature of the column was 60 to 85° C. (1° C./min) or to 110° C. (5° C./min). The temperature of a vaporizing chamber and a flame ionization detector (FID) was 230° C. From the area of a peak obtained under such analyzing conditions, the optical purity was calculated. A time during which each enantiomer of 1,1,1-trifluoro-2-propanol was maintained was 22.1 min in the case of R-configuration, and 23.9 min in the case of S-configuration.

EXAMPLE 2

Results of Examination (Screening) of Reactivity to 1,1,1-Trifluoroacetone

A liquid medium was prepared (at pH 6.5) to be composed of 1000 ml of an ion-exchanged water, 10 g of glucose, 5 g of polypeptone, 3 g of yeast extract, 3 g of malt extract, 3 g of potassium dihydrogenphosphate and 2 g of dipotassium hydrogen phosphate. The liquid medium was charged into test tubes (φ1.4 cm×18 cm) in an amount of 5 ml each, and then subjected to steam sterilization at 121° C. for 20 minutes.

These liquid media were inoculated with microorganisms shown in Table 4 and then shake culture was conducted thereon at 30° C. for 24 hours, thereby preparing suspensions ranging from $1.0\times10^9$ to $5.0\times10^9$ cfu/ml. To each of the cell suspensions, 5% (250 μl) of 1,1,1-trifluoroacetone and 250 μl of a 20% glucose aqueous solution were added, and then shake culture was conducted thereon at 30° C. for 24 hours to develop reaction. After the reaction, n-butyl acetate was added to each reaction solution, followed by extraction two times. Thereafter, the optical purity of a product was measured by gas chromatography (a column: BGB-174 (30 m×0.25 mm×0.25 mm) manufactured at BGB Analytik AG), the result of which is shown in Table 4.

Meanwhile, the above-mentioned reaction operation was conducted separately on the cell suspensions prepared under the conditions as discussed in the present example, with the exception that glucose was not added. Then the optical purity of a product was measured by the above-discussed analyzing method, the result of which is also shown in Table 4.

TABLE 4

| | | A*1 | | | B*2 | | |
|---|---|---|---|---|---|---|---|
| Microorganism | Accession Number | Yield (%) | Optical Purity (% ee) | Absolute Configuration | Yield (%) | Optical Purity (% ee) | Absolute Configuration |
| *Pichia anomala* | NBRC0120 | 12 | 100 | S | 15 | 100 | S |
| *Hansenula polymorpha* | NBRC0799 | 72 | 94 | S | 76 | 94 | S |
| *Candida parapsilosis* | NBRC0708 | 50 | 100 | S | 69 | 95 | S |
| *Candida mycoderma* | NBRC1247 | 23 | 88 | S | 19 | 100 | S |
| *Pichia naganishii* | NBRC1670 | 31 | 100 | S | 49 | 95 | S |

*1 Examinations where the reaction was conducted with the addition of glucose
*2 Examinations where the reaction was conducted without the addition of glucose Thus, it can be confirmed from above that (S)-1,1,1-trifluoro-2-propanol was produced with high enantiomeric excess in any cases using *Pichia anomala* NBRC0120, *Hansenula polymorpha* NBRC0799, *Candida parapsilosis* NBRC0708, *Candida mycoderma* NBRC1247 and *Pichia naganishii* NBRC1670.

Hereinafter, a result of a reaction in which 1,1,1-trifluoroacetone was so added that its total amount relative to the cell suspension was 2% (w/v) (Example 3) or 5% (w/v) (Example 4) will be discussed, the reaction being performed by using *Hansenula polymorpha* NBRC0799 that is capable of providing the target compound with high optical purity and high yield and selected among the microorganisms discussed in Example 1 and Example 2.

EXAMPLE 3

Production of (S)-1,1,1-Trifluoro-2-Propanol (2% (w/v))

A liquid medium was prepared to be composed of 2000 ml of an ion-exchanged water, 40 g of glucose, 20 g of peptone, 12 g of yeast extract, 12 g of malt extract, 12 g of potassium dihydrogenphosphate and 8 g of dipotassium hydrogen phosphate. The liquid medium was charged into a fermenter of 5 L capacity (available from B.E. MARUBISHI Co., Ltd. under the trade name of a MDN-type 5L(S)) and then subjected to steam sterilization at 121° C. for 60 minutes. This liquid medium was inoculated with 80 ml of a suspension of *Hansenula polymorpha* NBRC0799, the suspension being obtained by conducting a preliminary culture on 100 ml of the same composition to be $1.4\times10^9$ cfu/ml. Then, it was cultured at 28° C., an air ventilation of 1 vvm and a stirring speed of 500 rpm for 24 hours, thereby preparing a suspension of $1.7\times10^9$ cfu/ml (or 41 g/L in terms of the weight of wet cell bodies). At this time, adjustment of pH was attained by using aqueous ammonia, so that a pH was adjusted at 6.5. After culture had terminated, the ventilation amount and the stirring speed were changed to 0.1 vvm and 50 rpm. A solution obtained by dissolving 50.08 g of 1,1,1-trifluoroacetone and 90 g of glucose in 200 ml of an ion-exchanged water prepared in another vessel was sequentially added to the cell suspension by using a peristaltic pump. By monitoring the reduction of the substrate due to the microorganism every 24 hours, it was confirmed that the yield obtained after a lapse of 78 hours was 79.1%. This reaction solution was recalled in a 3 L Erlenmeyer flask and allowed to stand still at 20° C. for 5 days to develop a further reaction. The yield obtained after a lapse of 5 days was 91.4%.

In order to recall 1,1,1-trifluoro-2-propanol produced from the reaction solution after termination of the reaction, distillation was performed. A distillate was recalled in an amount of 344 ml, from which it was found, by internal standard method of $^{19}$F-NMR, that 44.72 g of 1,1,1-trifluoro-2-propanol was contained. As a result of measuring the optical purity under the above-discussed analyzing conditions, the optical purity was confirmed to be 98.7% ee (S-configuration).

EXAMPLE 4

Production of (S)-1,1,1-Trifluoro-2-Propanol (5% (w/v))

A liquid medium was prepared to be composed of 2000 ml of an ion-exchanged water, 60 g of glucose, 30 g of peptone, 50 g of yeast extract, 4.8 g of potassium dihydrogenphosphate and 2.5 g of dipotassium hydrogen phosphate. The liquid medium was charged into a fermenter of 5 L capacity (available from B.E. MARUBISHI Co., Ltd. under the trade name of a MDN-type 5L(S)) and then subjected to steam sterilization at 121° C. for 60 minutes. This liquid medium was inoculated with 80 ml of a suspension of *Hansenula polymorpha* NBRC0799, the suspension being obtained by conducting a preliminary culture on 100 ml of the same composition to be $2.0 \times 10^9$ cfu/ml. Then, it was cultured at 28° C., an air ventilation of 1 vvm and a stirring speed of 500 rpm for 24 hours, thereby preparing a suspension of $4.3 \times 10^9$ cfu/ml (or 86 g/L in terms of the weight of wet cell bodies). At this time, adjustment of pH was attained by using aqueous ammonia, so that a pH was adjusted at 6.5. After culture had terminated, the ventilation amount and the stirring speed were changed to 0.1 vvm and 50 rpm. A solution obtained by dissolving 125.2 g of 1,1,1-trifluoroacetone and 200 g of glucose in 300 ml of an ion-exchanged water prepared in another vessel was added to the suspension automatically by a computer program in the use of an online sugar concentration sensor (an online biosensor available from ABLE & Biott Co., Ltd. under the trade name of BF-410), so as to maintain a glucose concentration of 2%. It was confirmed that the yield obtained after a lapse of 168 hours was 94.9% by monitoring the reduction of the substrate due to the microorganism every 24 hours, upon which the reaction was terminated.

In order to recall 1,1,1-trifluoro-2-propanol produced from the reaction solution after termination of the reaction, distillation was performed. A distillate was recalled in an amount of 188 ml, from which it was found, by internal standard method of $^{19}$F-NMR, that 109.2 g of 1,1,1-trifluoro-2-propanol was contained. As a result of measuring the optical purity under the above-discussed analyzing conditions, the optical purity was confirmed to be 98.7% ee (S-configuration).

EXAMPLE 5

Production of (S)-1,1,1-Trifluoro-2-Propanol (5% (w/v), 1000 L-Scale)

For a pre-preliminary culture, a liquid medium was prepared to be composed of 200 ml of water, 6 g of glucose, 3 g of peptone, 5 g of yeast extract, 0.48 g of potassium dihydrogenphosphate and 0.25 g of dipotassium hydrogen phosphate. The liquid medium was charged into a 500 mL Erlenmeyer flask equipped with a baffle, and then subjected to steam sterilization at 121° C. for 15 minutes. This liquid medium was inoculated with 2 ml of a microbial species which is in freeze storage, of *Hansenula polymorpha* NBRC0799. Then, it was cultured at 28° C. and 160 rpm for 72 hours in the use of a rotary shaker, thereby preparing a cell suspension of $1.6 \times 10^9$ cfu/ml.

For a preliminary culture, 5000 ml of a liquid medium prepared at the same compositional ratios was charged into a fermenter of 10 L capacity (available from B.E. MARUBISHI Co., Ltd.) and then subjected to steam sterilization at 121° C. for 60 minutes. This liquid medium was inoculated with 180 ml of the cell suspension prepared by the pre-preliminary culture. Then, it was cultured at 28° C., an air ventilation of 1 vvm and a stirring speed of 250 rpm for 27 hours, thereby preparing a suspension of $1.2 \times 10^9$ cfu/ml. Adjustment of pH during culture was attained by using aqueous ammonia, so that a pH was adjusted at 6.5.

As a 1000 L fermenter for carrying out a main culture therein, there was used a culture apparatus of a ventilating and stirring type, available from Komatsugawa Chemical Engineering Co., Ltd. A culture tank was charged with 370 L of water, in which 9 kg of yeast extract, 6 kg of peptone, 0.96 kg of potassium dihydrogenphosphate and 0.5 kg of dipotassium hydrogen phosphate were dissolved, followed by steam sterilization at 121° C. for 60 minutes. A glucose solution prepared in another vessel to contain 30 L of water and 13 kg of a water-containing crystalline glucose was charged thereinto, and then inoculated with 5000 ml of the cell suspension prepared by the preliminary culture, followed by cultivation at 28° C., an air ventilation of 100 L/min and a stirring speed of 200 rpm for 24 hours. The ventilation amount and the stirring speed were changed to 20 L/min and 50 rpm, and then an aqueous solution prepared in another vessel by dissolving 25 kg of 1,1,1-trifluoroacetone and 43.5 kg of a water-containing crystalline glucose in 56.5 kg of an ion-exchanged water was added to the cell suspension that had been grown to $2.7 \times 10^9$ cfu/ml by termination of cultivation, in such a manner as to maintain a glucose concentration of 2% while suitably measuring the sugar concentration. Upon having confirmed that the conversion rate was 91.4% after a lapse of 168 hours by monitoring the reduction of the substrate due to the microorganism every 24 hours, the reaction was terminated. The pH during culture and reaction was adjusted at 6.5 by using aqueous ammonia.

The reaction solution obtained after the reaction was analyzed according to internal standard method of $^{19}$F-NMR, from which it was found that 13 kg of 1,1,1-trifluoro-2-propanol was contained. As a result of measuring the optical purity under the above-discussed analyzing conditions, the optical purity was confirmed to be 97.4% ee (S-configuration).

The invention claimed is:
1. A method for producing (S)-1,1,1-trifluoro-2-propanol represented by the formula [2], the method comprising the steps of:
reacting a microorganism with 1,1,1-trifluoroacetone represented by the formula [1], the microorganism being found in nature and used in a natural state,

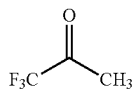
[2]

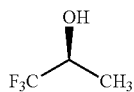
[1]

wherein at least one kind of microorganism, which is selected from the group consisting of *Hansenula polymorpha, Pichia anomala, Candida parapsilosis, Candida mycoderma, Pichia naganishii, Candida saitoana, Cryptococcus curvatus, Saturnospora dispora, Saccharomyces bayanus* and *Pichia membranaefaciens*, is used as the microorganism, by preparing a suspension of the microorganism having a density between $10^7$ and $10^{11}$ cfu/ml and adding 1,1,1-trifluoroacetone to the suspension so that the 1,1,1-trifluoroacetone has a concentration between 0.05 and 3% (w/v).

2. A method for producing (S)-1,1,1-trifluoro-2-propanol, as claimed in claim 1, wherein the microorganism is provided with an accession number as shown below

| Microorganism | Accession Number |
|---|---|
| *Hansenula polymorpha* | NBRC0799, ATCC26012 |
| *Pichia anomala* | NBRC0120 |
| *Candida parapsilosis* | NBRC0708 |
| *Candida mycoderma* | NBRC1247 |
| *Pichia naganishii* | NBRC1670 |
| *Candida saitoana* | NBRC0380 |
| *Cryptococcus curvatus* | NBRC1159 |
| *Saturnospora dispora* | NBRC0035 |
| *Saccharomyces bayanus* | NBRC0676 |
| *Pichia membranaefaciens* | NBRC0128. |

3. A method for producing (S)-1,1,1-trifluoro-2-propanol, as claimed in claim 1, wherein the reaction temperature is within a range between 20 and 30° C.

4. A method for producing (S)-1,1,1-trifluoro-2-propanol, as claimed in claim 1, wherein the pH during the reaction is within a range between 6.0 and 9.0.

5. A method for producing (S)-1,1,1-trifluoro-2-propanol, as claimed in claim 1, further comprising regenerating a coenzyme NAD(P)H used in the reacting step by virtue of a dehydrogenase of the microorganism itself, without adding the coenzyme NAD(P)H from the outside.

6. A method for producing (S)-1,1,1-trifluoro-2-propanol, as claimed in claim 5, further comprising using glucose as a substrate for the dehydrogenase in regeneration of the coenzyme NAD(P)H.

7. A method for producing (S)-1,1,1-trifluoro-2-propanol, as claimed in claim 1, wherein the density of the microorganism is $10^8$ to $10^{10}$ cfu/ml.

* * * * *